United States Patent [19]

Sauer et al.

[11] Patent Number: 5,411,966
[45] Date of Patent: May 2, 1995

[54] 2, 13-DISUBSTITUTED ERGOLINES, THEIR PRODUCTION AND USE IN PHARMACEUTICAL AGENTS

[75] Inventors: Gerhard Sauer; Bernd Schröter; Thomas Brumby; Helmut Wachtel; Peter A. Löschmann, all of Berlin, Germany

[73] Assignee: Schering Aktiengesellschaft, Bergkamen, Germany

[21] Appl. No.: 126,671

[22] Filed: Sep. 27, 1993

Related U.S. Application Data

[63] Continuation of Ser. No. 761,795, Sep. 16, 1991, abandoned.

[30] Foreign Application Priority Data

Jan. 15, 1990 [DE] Germany .......... 40 01 323.5

[51] Int. Cl.$^6$ .................. C07D 457/12; A61K 31/48
[52] U.S. Cl. ........................ 514/288; 546/66; 546/68
[58] Field of Search .............. 546/66, 68; 514/288

[56] References Cited

U.S. PATENT DOCUMENTS 4,137,315  1/1979  Farge et al. .......... 546/66

Primary Examiner—Johann Richter
Assistant Examiner—Catherine S. Kilby Scalzo
Attorney, Agent, or Firm—Millen, White, Zelano, & Branigan

[57] ABSTRACT

Compounds of formula I and their acid addition salts

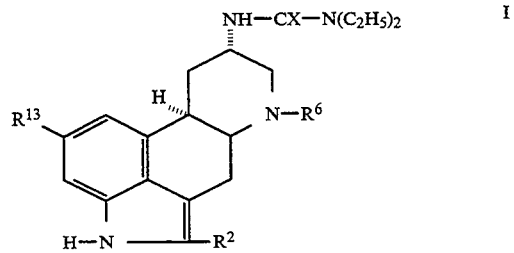

in which $R^2$ $R^6$ $R^{13}$ and X have the meanings defined herein are described as well as a process and intermediates for their production, and pharmaceutical agents containing these compounds.

21 Claims, No Drawings

2,13-DISUBSTITUTED ERGOLINES, THEIR PRODUCTION AND USE IN PHARMACEUTICAL AGENTS

This application is a continuation, of application Ser. No. 07/761,795, filed Sep. 16, 1991 abandoned.

SUMMARY OF THE INVENTION

The invention relates to new 2,13-disubstituted ergolines, their production and use in pharmaceutical agents, as well as intermediate products for their production.

13-Substituted ergolines, which exhibit affinity for central dopamine receptors, are known from EP-A-220 129. The new 2,13-disubstituted ergolines show a greater affinity for the dopamine receptor with improved metabolic stability and thus an increase of action.

The invention relates to compounds of formula I and their acid addition salts

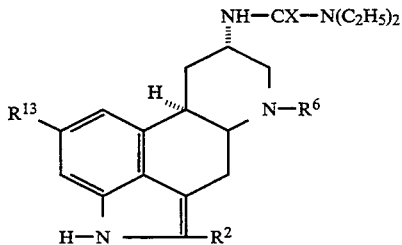

which
$R^2$ is halogen, $C_{1-6}$ alkyl or —S—$C_{1-4}$ alkyl,
$R^6$ is $C_{1-6}$ alkyl, $C_{3-6}$alkenyl or $C_{3-5}$cycloalkyl-$C_{1-2}$ alkyl,
X is oxygen or sulfur,
$R^{13}$ is chlorine, iodine, —S—$C_{1-4}$alkyl, $C_{1-6}$alkyl, $C_{2-6}$alkenyl, 1,3-dithiolan-2-yl, —CO—$R^3$ or —CR$^{4+}$R$^5$OH and $R^3$, $R^4$ and $R^5$ each mean hydrogen or $C_{1-5}$ alkyl The physiologically compatible acid addition salts are derived from the known inorganic and organic acids, such as, for example, hydrochloric acid, sulfuric acid, hydrobromic acid, citric acid, maleic acid, fumaric acid, tartaric acid, i.a.

Halogen contains in particular chlorine, bromine and iodine.

By alkyl is understood respectively a straight-chain or branched alkyl radical, such as, for example, methyl, ethyl, n-propyl, isopropyl, n-butyl, isobutyl, sec-butyl, tert-butyl, pentyl, hexyl, 2,2-dimethylpropyl, 2-methylbutyl, isopentyl, i.a.

If $R^6$ or $R^{13}$ means an alkenyl radical, the radical can be straight-chain or branched and contains preferably only one double bond, and the double bond in $R^6$ cannot be adjacent to the nitrogen atom. For example, vinyl, 1-propenyl, 2-propenyl, 1-methyl-2-propenyl, 1-butenyl, methallyl, are suitable as alkenyl radicals.

If $R^6$ means a cycloalkyl-alkyl group, radicals with up to 5 carbon atoms, for example, cyclopropylmethyl, cyclopropylethyl and cyclobutylmethyl, are preferred.

If $R^2$ $R^6$ and $R^{13}$ mean alkyl or alkenyl radicals, those with up to 4 carbon atoms are to be considered as preferred.

The compounds of formula I can occur as E or Z isomers or, if a chiral center is present in radical $R^2$ or $R^{13}$ as diastereomers and as their mixtures. The isomers and mixtures of isomers are also encompassed by this invention.

The compounds of formula I as well as their acid addition salts are usable as pharmaceutical agents because of their affinity for central dopamine receptors. Depending on the type of substituents in 2-, 13- and 6-position, they are dopaminergic agonistically, antagonistically or partially agonistically effective and are suitable, for example, for treatment of Parkinson's disease, hyperprolactinemia, positive or negative symptoms and signs in schizophrenia or emesis.

The dopaminergic agonistic effect is determined, for example, with the help of the method, described by Horowski, of the automatic registration of stereotypes in rats (Arzneim. Forsch. [Research on Pharmaceutical Agents] 12, 2281–2286, 1978): immediately after intraperitoneal test substance or vehicle administration, male Wistar rats (90–120 g) are placed individually in restrictive cages made from acrylic glass. By an electrodynamic recording system fastened in front of the head of the animals, the number of contacts on a steel beaker with a central metal rod as a result of the stereotyped chewing, licking and gnawing movements is registered for 60 minutes. The mean values ±SEM of the number of contacts over 60 minutes are calculated for the various treatment groups, each of which consists of 12 animals, and the significance of the differences between the mean values of the various test substance doses in comparison with the vehicle-treated control group is determined with the help of simple analysis of variance in connection with the Dunnett test. The results are explained in table 1.

TABLE 1

Triggering of stereotypes in rats for 60 minutes after intraperitoneal treatment with vehicles or various doses of ergoline urea derivatives
(x: p is less than 0.05, xx: p is less than 0.01, Analysis of variance/Dunnett Test vs. control; n: number of animals)

| | n | Control | 0.025 | 0.1 | 0.39 | 1.56 | 6.25 |
|---|---|---|---|---|---|---|---|
| | | | | Stereotypes (counts per 60 minutes) mean value ± SEM | | | |
| | | | | Test substance dose (mg/kg) | | | |
| A | 12 | 624 ± 101 | 617 ± 124 | 2582 ± 517 | 5834 ± 951xx | 7563 ± 804xx | 6948 ± 1090xx |
| B | 12 | 928 ± 120 | 1373 ± 448 | 1896 ± 270 | 5060 ± 607xx | 6929 ± 872xx | 4720 ± 970xx |
| C | 10 | 944 ± 84 | 1176 ± 183 | 1482 ± 170 | 5674 ± 662xx | 6594 ± 1128xx | 7111 ± 711xx |

A = 1,1-Diethyl-3-(2,13-dimethyl-6-propyl-8alpha-ergolinyl)-urea
B = 1,1-Diethyl-3-(13-ethyl-2-methyl-6-propyl-8alpha-ergolinyl)-urea
C = 8alpha-(3,3-Diethylureido)-2-methyl-6-propyl-ergoline-13-carbaldehyde Since the compounds according to the invention are distinguished in particular by dopaminergic agonistic action, they are suitable in particular for treatment of Parkinson's disease.

To use the compounds according to the invention as pharmaceutical agents, the compounds are brought into the form of a pharmaceutical preparation, which, in addition to the active ingredient for enteral or parenteral administration, contains suitable pharmaceutical, organic or inorganic inert vehicles, such as, for example, water, gelatin, gum arabic, lactose, starch, magnesium stearate, talc, vegetable oils, polyalkylene glycols, etc. The pharmaceutical preparations can be present in solid form, for example, as tablets, coated tablets, suppositories, capsules, or in liquid form, for example, as solutions, suspensions or emulsions. Optionally, they also contain auxiliary agents, such as preservatives, stabilizers, wetting agents or emulsifiers, salts to change the osmotic pressure or buffers.

The compounds according to the invention are introduced in a dose of 0,001 to 10 mg of active substance in a physiologically compatible vehicle. The use of the compounds according to the invention takes place in a dose of 0.00001 to 0.1 mg/kg/day, preferably 0.001 to 0.1 mg/kg/day analogously to the known agent bromocryptine.

The production of the compounds of formula I according to the invention can also be performed according to methods known in the art.

For example, compounds of formula I are attained, by
a) compounds of formula II

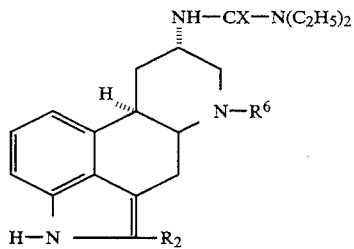

in which $R^2$ $R^6$ and X have the above-named meaning, being reacted in the presence of an acid with an electrophilic agent or
b) compounds of formula III

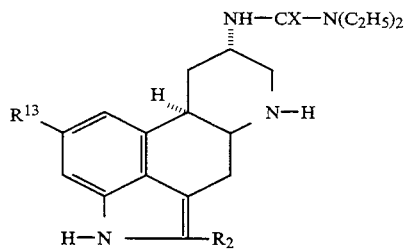

in which $R^2$, $R^{13}$ and X have the above-named meaning, being alkylated or alkenylated to compounds with $R^6$ in the above-named meaning and then optionally alpha) compounds with $R^{13}=$—CO—$R^3$ with $R^3$ in the above-named meaning being reduced to compounds with $R^{13}=$—$CR^4R^5$OH and the latter optionally being dehydrated to compounds with $R^{13}=C_{2-6}$ alkenyl or reduced to compounds with $R^{13}=$—$C_{1-6}$ alkyl or beta) compounds with $R^{13}=$1,3-dithiolan-2-yl being converted to compounds with $R^{13}=$—CHO or $CH_3$ or
gamma) urea being converted to thiourea or
delta) the isomers being separated or the acid addition salts being formed.

The electrophilic substitution in 13-position according to process a) is performed in the presence of an acid at temperatures of 0° C. to 20° C. and is generally completed after 1 to 24 hours.

Inorganic acids, such as phosphoric acid, sulfuric acid, organic acids, such as trifluoroacetic acid, methanesulfonic acid, acetic acid, and Lewis acids, such as aluminum chloride, titanium chloride, dimethylaluminum chloride, tin(IV) chloride, boron fluoride, i.a., can be used as acids, and the organic acid can be used as solvent or inert aprotic solvents, such as chlorinated hydrocarbons, such as dichloromethane, chloroform, tetrachloroethane or nitrobenzene, are added.

Suitable electrophiles are, for example: acyl chlorides, such as acetyl chloride, propionyl chloride; halogenation agents, such as N-chlorosuccinimide, N-iodosuccinimide, trichloroisocyanuric acid; dimethylmethylthio-sulfonium tetrafluoroborate; dichloromethyl alkyl ether; chloroformic acid alkyl ester; formic acid alkyl ester and ethanedithiol or dithiolane, i.a.

The substitution in 6-position according to process b) can be performed, for example, according to A. Cerny et al. Coll. Czech. Chem. Comm. 49, 2828 (1984) or according to the process described in EP-21206, by the 6-H compound of formula II being reacted with the corresponding $R^6$ halides (bromides, chlorides, iodides). The reaction suitably takes place in an inert solvent such as ethanol, dimethylformamide, acetonitrile or nitromethane in the presence of bases such as DBU, alkali hydroxides or alkali carbonates.

Compounds of formula I with $R^{13}$ meaning a —$COR^3$ group can be reduced to alcohol according to the usual processes, such as, for example, with lithium aluminum hydride or lithium tri-tertbutoxyalanate in an aprotic solvent, such as cyclic or acyclic ethers, for example, tetrahydrofuran, dioxane, and diethyl diethyl ether. 1-Hydroxy-alkylated substituents $R^{13}$ can also be produced by Grignardation or lithium alkylation. The Grignardation can take place with the usual Grignard reagents, such as alkyl magnesium halides in an aprotic solvent, such as cyclic and acyclic ethers at temperatures of −70° C. to 20° C. The reaction with alkyl lithium takes place under analogous conditions.

The subsequent dehydration for the double bond can be performed in the usual way, such as, for example, with sulfonates or acetates in polar solvents, such as ethers in the presence of a base and optionally with heating.

The reduction of the alcohols to 13-alkyl derivatives can take place, for example, by reaction with $NaBH_4$ in acetic acid or by reduction with lithium in ammonia.

To introduce the 13—$CH_3$ group, it can be advantageous, before the reduction of the 13—$CH_2$-OH radical, to esterify this radical with acids, such as pivalic acid, acetic acid, benzoic acid and then to reduce it according to the known processes as described in German patent application P 4020341.7.

If $R^{13}$ means a dithiolane radical, it can be converted to the 13-formyl derivative, for example, by aqueous $SiO_2$ treatment and subsequent reaction with sulfuryl chloride in aprotic solvents, such as chlorinated hydrocarbons. The 13-methyl derivative can be produced by reaction with Raney nickel at room temperature in protic solvents such as alcohols.

The conversion of the urea derivatives to the thioureas can take place, for example, according to the process described in EP-A-217730 by reaction with phosphorus oxychloride and a thiolation agent.

The mixture of isomers can be separated according to the usual methods, such as, for example, crystallization, chromatography or salt formation in the diastereomers or E/Z isomers.

The compounds of formula I are isolated either as free bases or in the form of their physiologically compatible acid addition salts.

For the formation of salts, a compound of formula I is dissolved, for example, in a little alcohol or methylene chloride and mixed with a concentrated solution of the desired acid.

The introduction of the substituents in 6-position can take place before or after substitution in 13-position. The invention also comprises the compounds of $$\text{(IV)}$$

in which $R^2$, $R^{13}$ and X have the above-named meaning.

The compounds of formula IV represent valuable intermediate products for the production of pharmacologically effective compounds. The reduction of 6-cyanoergoline to the 6-H compound takes place, for example, according to A. Cerny et al. Coll. Czech. Chem. Comm. 49, 2828 (1984). The conversion of the intermediate products to the active substance takes place according to the method described in process variant b).

In so far as the production of the initial compounds is not described, these compounds are known or can be produced analogously to known compounds or to the processes described here.

The following examples are to explain the process according to the invention.

EXAMPLES

Example 1

1,1-Diethyl-3-[13-(1,3-dithiolan-2-yl)-2,6-dimethyl-8alphaergolinyl]-urea 5.31 g of 1,1-diethyl-3-(2,6-dimethyl-8alpha-ergolinyl)-urea (15 mmol) is dissolved in 150 ml of chloroform and 50 ml of formic acid ethyl ester, 2.8 ml of ethanedithiol (33 mmol) and 60 ml of a 1 molar solution of titanium tetrachloride in dichloromethane (60 mmol) are added and stirred for 20 hours at room temperature. Then, it is mixed with 40 ml of methanol and 300 ml of water, made alkaline with 30 ml of 25% ammonia solution and shaken out with dichloromethane. The organic phases are dried with sodium sulfate, concentrated by evaporation and the residue is chromatographed on silica gel with dichloromethane/methanol. 4.14 g of substance, which crystallizes from ethyl acetate, is isolated, $[\alpha]_D = -4°$ (0.5 % in chloroform).

Analogously, there are produced:

1,1-Diethyl-3-[13-(1,3-dithiolan-2-yl)-2-methyl-6-propyl-8alpha-ergolinyl]-urea from 1,1-diethyl-3-(2-methyl-6-propyl-8alpha-ergolinyl)-urea, in 38% yield.

1,1-diethyl-3-[13-(1,3-dithiolan-2-yl)-2-ethyl-6-propyl-8alpha-ergolinyl]-urea from 1,1-diethyl-3-(2-ethyl-6-propyl-8alpha-ergolinyl)-urea, in 28% yield.

Example 2

8alpha-3,3-Diethylureido)-2,6-dimethyl-ergoline-13-carbaldehyde 3.26 g of 1,1-diethyl-3-[13-(1,3-dithiolan-2-yl)-2,6-dimethyl-8alpha-ergolinyl]-urea (7.1 mmol) is dissolved in 35 ml of chloroform and mixed with 5.3 g of silica gel and 5.7 ml of water. Then, the solution of 1.37 ml of sulfuryl chloride (17 mmol) is instilled in 35 ml of chloroform within 10 minutes and stirred for 1 hour at room temperature. After adding 8.5 g of potassium carbonate, it is stirred for 15 minutes, some ethanol and saturated common salt solution are added and shaken out with dichloromethane. The organic phases are dried and concentrated by evaporation, the residue is chromatographed on silica gel with ethyl acetate/methanol, yield 1.45 g. This substance is crystallized from ethyl acetate/diisopropyl ether, yield 1.09 g (40% of theory), $[\alpha]_D = -9°$ (0.5% in chloroform).

Analogously, there are produced:

8alpha-(3,3-Diethylureido)-2-methyl-6-propyl-ergoline-13-carbaldehyde from 1,1-diethyl-3-[13-(1,3-dithiolan-2-yl)-2-methyl-6-propyl-8alpha-ergolinyl]-urea, yield 51%.

8alpha-(3,3-diethylureido)-2-ethyl-6-propyl-ergoline-13-carbaldehyde from 1,1-diethyl-3-[13-(1,3-dithiolan-2-yl)-2-ethyl- -6-propyl-8alpha-ergolinyl]-urea, in 62% yield.

Example 3

2-Bromo-8alpha-(3,3-diethylureido)-6-methyl-ergoline-13-carbaldehyde 838 mg of 3-(2-bromo-6-methyl-8alpha-ergolinyl)-1,1-diethylurea (2 mmol) is dissolved in 100 ml of dichloromethane, 1.2 g of anhydrous aluminum chloride (9 mmol) and 1.8 ml of dichloromethyl methyl ether (20 mmol) are added and stirred for 15 minutes at room temperature. The reaction mixture is mixed with ice and, after 15 minutes, with a solution of 1.5 g of tartaric acid in 50 ml of water and made alkaline with 5 ml of conc. ammonia solution. It is extracted with dichloromethane, the organic phases are dried with sodium sulfate and the solvent is distilled off. The residue is chromatographed on silica gel with dichloromethane/methanol, 406 mg (45% of theory) is isolated.

Analogously, there are produced:

2-Bromo-8alpha-(3,3-diethylureido)-6-propyl-ergoline-13-carbaldehyde from 3-(2-bromo-6-propyl-8alpha-ergolinyl)-1,1-diethylurea, yield 27%.

2-chloro-8alpha-(3,3-diethylureido)-6-methyl-ergoline-13-carbaldehyde from 3-(2-chloro-6-methyl-8alpha-ergolinyl)-1,1-diethylurea, in 37% yield.

2-chloro-8alpha-(3,3-diethylureido)-6-propyl-ergoline-13-carbaldehyde from 3-(2-chloro-6-propyl-8alpha-ergolinyl)-1,1-diethylurea, in 32% yield.

8alpha-(3,3-diethylureido)-2-methylthio-6-propyl-ergoline- 13-carbaldehyde from 1,1-diethyl-3-(2-methylthio-6-propyl-8alpha-ergolinyl)-urea, in 42% yield.

Example 4

1,1-Diethyl-3-(2,6-dimethyl-13-hydroxymethyl-8alpha-ergolinyl)-urea 370 mg of 8alpha-(3,3-diethylureido)-2,6-dimethyl-ergoline-13-carbaldehyde (1 mmol) is dissolved in 50 ml of tetrahydrofuran and reduced with 200 mg of lithium aluminum hydride at room temperature for 1 hour. The mixture is cooled off in an ice bath and mixed in succession with 0.2 ml of water, 0.2 ml of 15% sodium hydroxide solution and 0.6 ml of water, the precipitate is filtered off and the filtrate is evaporated to dryness. The residue is chromatographed on silica gel with dichloromethane/methanol. 243 mg of alcohol, which crystallizes from ethyl acetate, is isolated. Yield 166 mg (44% of theory), $[\alpha]_D = +6°$ (0.5% in chloroform).

Analogously, there are produced from the respective aldehydes:

1,1-Diethyl-3-(13-hydroxymethyl-2-methyl-6-propyl-8alpha-ergolinyl)-urea, yield 73%.
1,1-diethyl-3-(2-ethyl-13-hydroxymethyl-6-propyl-8alpha-ergolinyl)-urea, yield 43%.
3-(2-bromo-13-hydroxymethyl-6-methyl-8alpha-ergolinyl)-1,1-diethylurea, yield 51%.
3-(2-bromo-13-hydroxymethyl-6-propyl-8alpha-ergolinyl)-1,1-diethylurea, yield 62%.
3-(2-chloro-13-hydroxymethyl-6-propyl-8alpha-ergolinyl)-1,1-diethylurea, yield 42%.
1,1-diethyl-3-(13-hydroxymethyl-2-methylthio-6-propyl- 8alpha-ergolinyl)-urea, yield 34%.

Example 5

1,1-Diethyl-3-(2,6,13-trimethyl-8alpha-ergolinyl)-urea 458 mg of 1,1-diethyl-3-[13-(1,3-dithiolan-2-yl)-2,6-dimethyl-8alpha-ergolinyl)-urea (1 mmol) is dissolved in 50 ml of methanol and treated with several portions of Raney nickel at room temperature until the initial material has disappeared according to thin-layer chromatography. It is filtered by kieselguhr, the solvent is concentrated by evaporation and the residue is chromatographed on silica gel with dichloromethane/methanol, the isolated substance is crystallized from methanol, yield 117 mg (31% of theory).

Example 6

1,1-Diethyl-3-(2,6,13-trimethyl-8alpha-ergolinyl)-urea 715 mg of 1,1-diethyl-3-(2,6-dimethyl-13-hydroxymethyl- 8alpha-ergolinyl)-urea (1.5 mmol) is dissolved in 10 ml of pyridine and mixed with 2 ml of trimethylacetyl chloride. Ice is added after 30 minutes of stirring at room temperature, it is stirred for another 30 minutes, made alkaline with ammonia and the mixture is cooled in an ice bath. The precipitated crystals are suctioned off, yield 785 mg, $[\alpha]_D = -2°$ (0.5% in chloroform). The mother liquor is extracted with dichloromethane, dried and concentrated by evaporation. Both fractions are dissolved together in 6 ml of tetrahydrofuran and the solution is instilled in 50 ml of condensed, anhydrous ammonia. Then, it is mixed with 160 mg of lithium and the blue solution is stirred for 30 minutes at −40° C. Solid ammonium chloride, until decolorization, and 5 ml water are added in succession, the ammonia is evaporated and it is diluted with 80 ml of water. After 30 minutes of stirring in an ice bath, the precipitated crystals are suctioned off and dried in a vacuum, yield 643 mg (94% of theory), $[\alpha]_D = +3°$ (0.5% in chloroform).

From the respective alcohol, there are analogously produced:

1,1-Diethyl-3-(2,13-dimethyl-6-propyl-8alpha-ergolinyl)-urea, yield 76%.
1,1-diethyl-3-(2-ethyl-13-methyl-6-propyl-8alpha-ergolinyl)-urea, yield 81%.

Example 7

3-(13-Acetyl-2,6-dimethyl-8alpha-ergolinyl)-1,1-diethylurea 2.4 g of anhydrous aluminum chloride and 1.3 ml of acetyl chloride are dissolved in 70 ml of dichloromethane and stirred for 15 minutes at room temperature. 708 mg of 1,1-diethyl-3-(2,6-dimethyl-8alpha-ergolinyl)-urea (2 mmol) dissolved in 30 ml of dichloromethane is added to it, and stirred for 30 minutes at room temperature. Ice is added and after 15 minutes of stirring, a solution of 2.8 g of tartaric acid in 80 ml of water is added. After another 15 minutes, it is made alkaline with conc. ammonia, the organic phase is separated and the water phase is extracted. All organic phases are dried with sodium sulfate and concentrated by evaporation, the residue is chromatographed on silica gel with dichloromethane/methanol, yield 454 mg.

Analogously, there are produced:

3-(13-Acetyl-2-methyl-6-propyl-8alpha-ergolinyl)-1,1-diethylurea, yield 61%.
3-(13-acetyl-2-ethyl-6-methyl-8alpha-ergolinyl)-1,1-diethylurea, yield 38%.
3-(13-acetyl-2-ethyl-6-propyl-8alpha-ergolinyl)-1,1-diethylurea, yield 58%.
3-(13-acetyl-2-bromo-6-methyl-8alpha-ergolinyl)-1,1-diethylurea, yield 67%.
3-(13-acetyl-2-bromo-6-propyl-8alpha-ergolinyl)-1,1-diethylurea, yield 47%.
3-(13-acetyl-2-chloro-6-propyl-8alpha-ergolinyl)-1,1-diethylurea, yield 71%.
3-(13-acetyl-6-methyl-2-methylthio-8alpha-ergolinyl)-1,1-diethylurea, yield 44%, $[\alpha]_D = +7°$ (0.5% in chloroform).

Example 8

1,1-Diethyl-3-[2,6-dimethyl-13-(1-hydroxyethyl)-8alpha-erolinyl]-urea 406 mg of 3-(13-acetyl-2,6-dimethyl-8alpha-ergolinyl)-1,1-diethylurea (1 mmol) is reduced in 50 ml of tetrahydrofuran with 200 mg of lithium aluminum hydride as described in example 4, worked up and crystallized from ethyl acetate, yield 216 mg (53% of theory), $[\alpha]_D = +12°$ (0.1% in pyridine).

Analogously, the following alcohols are produced:

1,1-Diethyl-3-[13-(1-hydroxyethyl)-2-methyl-6-propyl-8alpha-ergolinyl]-urea, yield 75%.
1,1-diethyl-3-[2-ethyl-13-(1-hydroxyethyl)-6-propyl-8alpha-ergolinyl]-urea, yield 57%.
1,1-diethyl-3-[2-ethyl-13-(1-hydroxyethyl)-6-methyl-8alpha-ergolinyl]-urea, yield 43%.
3-[2-bromo-13-(1-hydroxyethyl)-6-methyl-8alpha-ergolinyl]-1,1-diethylurea, yield 51%.
3-[2-bromo-13-(1-hydroxyethyl)-6-propyl-8alpha-ergolinyl]-1,1-diethylurea, yield 61%.
3-[2-chloro-13-(1-hydroxyethyl)-6-propyl-8alpha-ergolinyl]-1,1-diethylurea, yield 47%.
1,1-diethyl-3-[13-(1-hydroxyethyl)-6-methyl-2-methylthio- 8alpha-ergolinyl]-urea, yield 63%.

Example 9

1,1-Diethyl-3-(13-ethyl-2,6,-dimethyl-8alpha-ergolinyl)-urea 280 mg of 1,1-diethyl-3-[2,6-dimethyl-13-(1-hydroxyethyl)- 8alpha-ergolinyl)-urea (0.7 mmol) is dissolved in 14 ml of acetic acid and stirred with 700 mg of sodium borohydride (tablets) for 15 minutes at room temperature. Then, ice is added, it is stirred for another 15 minutes and made alkaline with conc. ammonia. The substance is extracted with dichloromethane, the organic phases are dried and concentrated by evaporation, the residue is chromatographed on silica gel with dichloromethane/methanol. The isolated substance is crystallized from ethyl acetate/hexane. Yield 176 mg (65% of theory), $[\alpha]_D = +50°$ (0.5% in chloroform).

Analogously, the corresponding alcohols are reduced:

- 1,1-Diethyl-3-(13-ethyl-2-methyl-6-propyl-8alpha-ergolinyl)-urea, yield 73% of theory.
- 1,1-diethyl-3-(2,13-diethyl-6-methyl-8alpha-ergolinyl)-urea, yield 64% of theory.
- 1,1-diethyl-3-(2,13-diethyl-6-propyl-8alpha-ergolinyl)-urea, yield 47% of theory.
- 3-(2-bromo-13-ethyl-6-methyl-8alpha-ergolinyl)-1,1-diethylurea, yield 28%.
- 3-(2-bromo-13-ethyl-6-propyl-8alpha-ergolinyl)-1,1-diethylurea, yield 23%.
- 3-(2-chloro-13-ethyl-6-propyl-8alpha-ergolinyl)-1,1-diethylurea, yield 44%.
- 1,1-diethyl-3-(13-ethyl-2-methylthio-6-propyl-8alpha- ergolinyl)-urea, yield 33%.

Example 10

3-(2-Bromo-6,13-dimethyl-8alpha-ergolinyl)-1,1-diethylurea

From 3-(2-bromo-13-hydroxymethyl-6-methyl-8alpha-ergolinyl)-1,1-diethylurea by reduction as described in example 9, yield 43%.

Analogously, there are synthesized:

- 3-(2-Bromo-13-methyl-6-propyl-8alpha-ergolinyl)-1,1-diethylurea, yield 24%.
- 3-(2-chloro-13-methyl-6-propyl-8alpha-ergolinyl)-1,1-diethylurea, yield 45%.
- 1,1-diethyl-3-(13-methyl-2-methylthio-6-propyl-8alpha- ergolinyl)-urea, yield 37%.

Example 11

1,1-Diethyl-3-[13-(1-hydroxy-1-methyl-ethyl)-2,6-dimethyl 396 mg of 3-(13-acetyl-2,6-dimethyl-8alpha-ergolinyl)-1,1-diethylurea (1 mmol) is dissolved in 30 ml of dry tetrahydrofuran and the solution is cooled to −65° C. 0.8 ml of a 1.6 molar solution of methyllithium in ether is added (1.3 mmol), then the solution is allowed to warm to room temperature and is stirred for another 30 minutes. It is poured on ice, made alkaline with conc. ammonia solution and extracted with ethyl acetate. The organic phases are dried and evaporated, the residue is chromatographed on silica gel with dichloromethane/methanol, yield 285 mg (67% of theory).

Analogously, there are produced from the 13-acetyl compounds:

- 1,1-Diethyl-3-[13-(1-hydroxy-1-methyl-ethyl)-2-methyl-6-propyl-8alpha-ergolinyl]-1,1-urea, yield 54%.
- 3-[2-bromo-13-(1-hydroxy-1-methyl-ethyl)-6-propyl-8alpha-ergolinyl]-1,1-diethylurea, yield 73%.
- 3-[2-chloro-13-(1-hydroxy-1-methyl-ethyl)-6-propyl-8alpha- ergolinyl)-1,1-diethylurea, yield 67%.

Example 12

1,1-Diethy-3(2,6-dimethyl-13-isopropenyl-8alpha-ergolinyl)-urea 208 mg of 1,1-diethyl-3-[13-(1-hydroxy-1-methyl-ethyl)-2,6- -dimethyl-8alpha-ergolinyl]-urea (0.5 mmol) is dissolved in 20 ml of anhydrous tetrahydrofuran, mixed with 0.7 ml of triethylamine (5 mmol) and 0.4 ml of methanesulfonic acid chloride (5 mmol) and stirred for 30 minutes at room temperature. Ice is added to the mixture, it is made alkaline with conc. ammonia and shaken out with ethyl acetate. The residue is chromatographed on silica gel with dichloromethane/methanol, yield 99 mg (50% of theory).

Analogously, there are produced:

- 1,1-Diethyl-3-(13-isopropenyl-2-methyl-6-propyl-8alpha- ergolinyl)-urea, yield 34%.
- 3-(2-bromo-13-isopropenyl-6-propyl-8alpha-ergolinyl)-1,1-diethylurea, yield 45%.

Example 13

1,1-Diethyl-3-(2,6-dimethyl-13-isopropyl-8alpha-ergolinyl)-urea 1,1-Diethyl-3-[13-(1-hydroxy-1-methyl-1-ethyl)-2,6-dimethyl- 8alpha-ergolinyl]-urea (0.5 mmol) is dissolved in 5 ml of glacial acetic acid and 0.25 g of sodium borohydride is added. After 15 minutes of stirring at room temperature, ice is added, it is made alkaline with conc. ammonia and extracted with ethyl acetate. The organic phases are dried with sodium sulfate and concentrated by evaporation, the residue is chromatographed on silica gel with dichloromethane/methanol, yield 76 mg (38% of theory).

Analogously, there are produced:

- 1,1-Diethyl-3-(13-isopropyl-2-methyl-6-propyl-8alpha- ergolinyl)-urea, yield 47%.
- 3-(2-chloro-13-isopropyl-6-propyl-8alpha-ergolinyl)-1,1-diethylurea, yield 33%.

Example 14

3-(2-Bromo-13-chloro-6-methyl-8alpha-ergolinyl)-1,1-diethylurea, 2.1 g of 3-(2-bromo-6-methyl-8alpha-ergolinyl)-1,1-diethylurea (5 mmol) and 388 mg of trichloroisocyanuric acid (1.67 mmol) are dissolved in 100 ml of trifluoroacetic acid at room temperature. After 15 minutes, ice is added, it is made alkaline with conc. ammonia and shaken out with dichloromethane. The organic phases are dried and concentrated by evaporation, the residue is chromatographed and the product crystallizes from ethyl acetate/ether, yield 480 mg (21% of theory).

Analogously, there are produced:

- 3-(2-Bromo-13-chloro-6-propyl-8alpha-ergolinyl)-1,1-diethylurea, yield 38%.
- 3-(2,13-dichloro-6-propyl-8alpha-ergolinyl)-1,1-diethylurea, yield 33%.
- 3-(13-chloro-2-methyl-6-propyl-8alpha-ergolinyl)-1,1-diethylurea, yield 21%.
- 3-(13-chloro-2,6-dimethyl-8alpha-ergolinyl)-1,1-diethylurea, yield 28%.

3-(13-chloro-2-ethyl-6-propyl-8alpha-ergolinyl)-1,1-diethylurea, yield 41%.

Example 15

3-(2-Bromo-13-iodo-6-methyl-8alpha-ergolinyl)-1,1-diethylurea 42 mg of 3-(2-bromo-6-methyl-8alpha-ergolinyl)-1,1-diethylurea (0.1 mmol) is dissolved in 2 ml of trifluoroacetic acid and mixed with 22 mg of N-iodosuccinimide (0.1 mmol). After 15 minutes of stirring at room temperature, ice is added, it is made alkaline with ammonia, and shaken out with dichloromethane. The organic phases are dried and concentrated by evaporation, the residue is chromatographed. The pure substance crystallizes from dichloromethane, yield 9 mg (16% of theory).

Analogously, there are produced:
3-(2-Bromo-13-iodo-6-propyl-8alpha-ergolinyl)-1,1-diethylurea, yield 25%.
1,1-diethyl-3-(2,6-dimethyl-13-iodo-8alpha-ergolinyl)-urea, yield 17%.
1,1-diethyl-3-(13-iodo-2-methyl-6-propyl-8alpha-ergolinyl)-urea, yield 29%.

Example 16

1,1-Diethyl-3-(2,6.dimethyl-13-methylthio-8alpha-ergolinyl)-urea 3.54 g of 1,1-diethyl-3-(2,6-dimethyl-8alpha-ergolinyl)-urea (10 mmol) is dissolved in 200 ml of trifluoroacetic acid and mixed at intervals of 15 minutes in three portions each with 0.98 g of dimethyl-methylthio-sulfonium-tetrafluoroborate (15 mmol) at room temperature. After 15 minutes, the mixture is poured on ice, made alkaline with ammonia and shaken out with dichloromethane. The organic phases are dried with sodium sulfate and concentrated by evaporation, the residue is chromatographed on silica gel with dichloromethane/methanol/hexane. The substance is crystallized from ethyl acetate/hexane, yield 138 mg (4% of theory).

Analogously, there is produced:
1,1-Diethyl-3-(2-methyl-13-methylthio-6-propyl-8alpha- ergolinyl)-urea, yield 13%.

Example 17

1,1-Diethyl,3-(2,6,13-trimethyl-8alpha-ergolinyl)-thiourea 0.5 Ml of freshly distilled phosphorus oxychloride (5.6 mmol) and 368 mg of 1,1-diethyl-3-(2,6,13-trimethyl-8alpha- ergolinyl)-urea (1 mmol) are dissolved in 20 ml of dichloromethane at −20° C. and the mixture is allowed to stir overnight at room temperature. The volatile portions are now drawn off in a vacuum, the residue is dissolved in 40 ml of acetonitrile and mixed with a solution of 0.8 g of potassium xanthate (5.6 mmol) in 80 ml of acetonitrile. It is stirred for 2 hours at room temperature, then ice and conc. ammonia solution are added and shaken out with dichloromethane. The organic phases are dried with sodium sulfate and concentrated by evaporation, the residue is chromatographed on silica gel with ethyl acetate and crystallized from ethyl acetate/diisopropyl ether, yield 43%.

Analogously, the following thioureas are produced by thiolation of the ureas:
1,1-Diethyl-3-(2,13-dimethyl-6-propyl-8alpha-ergolinyl)-thiourea, yield 42%.
1,1-diethyl-3-(13-ethyl-2-methyl-6-propyl-8alpha-ergolinyl)-thiourea, yield 56%.
3-(13-chloro-2-methyl-6-propyl-8alpha-ergolinyl)-1,1-diethyl-thiourea, yield 37%.
1,1-diethyl-3-(2-ethyl-13-methyl-6-propyl-8alpha-ergolinyl)-thiourea.
3-(2-bromo-6,13-dimethyl-8alpha-ergolinyl)-1,1-diethylthiourea, yield 61%.
3-(2-bromo-13-methyl-6-propyl-8alpha-ergolinyl)-1,1-diethyl-thiourea, yield 34%.
3-(2-bromo-13-iodo-6-propyl-8alpha-ergolinyl)-1,1-diethyl-thiourea, yield 23%.
3-(2-bromo-13-chloro-6-propyl-8alpha-ergolinyl)-1,1-diethyl-thiourea, yield 59%.
3-(2-chloro-13-methyl-6-propyl-8alpha-ergolinyl)-diethyl-thiourea, yield 65%.
3-(2,13-dichloro-6-propyl-8alpha-ergolinyl)-1,1-diethyl-thiourea, yield 42%.
1,1-diethyl-3-(13-methyl-2-methylthio-6-propyl-8alpha- ergolinyl)-thiourea, yield 34%.

We claim:
1. A 2,13-disubstituted ergoline compound of formula I

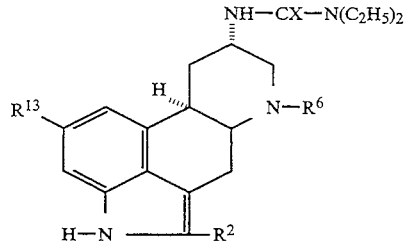

in which
$R^2$ is halogen, $C_{1-6}$ alkyl or —S—$C_{1-4}$ alkyl;
$R^6$ is $C_{1-6}$ alkyl, $C_{3-6}$ alkenyl or $C_{3-5}$ cycloalkyl-$C_{1-2}$ alkyli;
X is oxygen or sulfur;
$R^{13}$ is —S—$C_{1-4}$ alkyl, $C_{1-6}$ alkyl, $C_{2-6}$ alkenyl, 1,3-dithiolan-2-yl, —CO—$R^3$ or —C$R^4R^5$OH; and
$R^3$, $R^4$ and $R^5$ are each independently hydrogen or $C_{1-5}$ alkyl, or
a physioloqically compatible acid addition salt thereof,
with the proviso that said compound is not 3-(13-acetyl-2- bromo-6-methyl-8alpha-ergolinyl)-1,1-diethylurea.

2. A compound according to claim 1, wherein said compound is:
1,1-diethyl-3-(2,6,13-trimethyl-8alpha-ergolinyl)-urea or a physiological compatible acid addition salt thereof;
1,1-diethyl-3-(2,13-dimethyl-6-propyl-8alpha-ergolinyl)-urea or a physiologically compatible acid addition salt thereof;
1,1-diethyl-3-(13-ethyl-2,6-dimethyl-8alpha-ergolinyl)-urea or a physiologically compatible acid addition salt thereof;
1,1-diethyl-3-(13-ethyl-2-methyl-6-propyl-8alpha-ergolinyl)-urea or a physiologically compatible acid addition salt thereof;
1,1-diethyl-3-(2,6-dimethyl-13-isopropyl-8alpha-ergolinyl)-urea or a physioloqically compatible acid addition salt thereof;

3-(13-acetyl-2-methyl-6-propyl-8alpha-ergolinyl)-1,1-diethylurea or a physiologically compatible acid addition salt thereof;

8alpha-(3,3-diethylureido)-2-methyl-6-propyl-ergoline-13-carbaldehyde or a physiologically compatible acid addition salt thereof;

1,1-diethyl-3-(2,6-dimethyl-13-methylthio-8alpha-ergolinyl)-urea or a physiologically compatible acid addition salt thereof; or 1,1-diethyl-3-(2,13-dimethyl-6-propyl-8alpha-ergolinyl)-thiourea or a physioloqically compatible acid addition salt thereof.

3. A pharmaceutical composition comprising a pharmaceutically acceptable vehicle and an effective amount of a compound according to claim 1.

4. A compound of formula IV

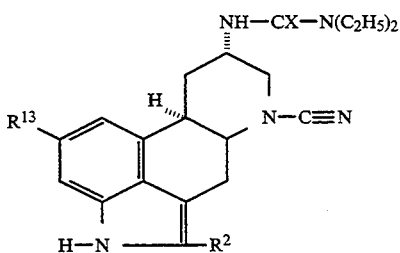

in which

R$^2$ is halogen, C$_{1-6}$-alkyl or —S—C$_{1-4}$-alkyl;
R$^{13}$ is —S—C$_{1-4}$-alkyl, C$_{1-6}$-alkyl, C$_{2-6}$-alkenyl, 1,3-dithiolan-2-yl, —CO—R$^3$ or —CR$^4$R$^5$OH;
R$^3$, R$^4$ and R$^5$ are each independently hydrogen or C$_{1-5}$-alkyl; and
X is oxygen or sulfur.

5. A compound according to claim 1, wherein R$^6$ is C$_{1-6}$-alkyl and X is oxygen.

6. A compound according to claim 1, wherein R$^{13}$ is C$_{1-6}$-alkyl, 1,3-dithiolan-2-yl, methylthio, carbaldehyde, hydroxymethyl, 1-hydroxyethyl, 1-hydroxy-1-methyl-ethyl, or C$_{2-6}$-alkenyl.

7. A compound according to claim 6, wherein R$^2$ is C$_{1-6}$-alkyl and R$^{13}$ is C$_{1-6}$-alkyl.

8. A compound according to claim 7, wherein R$^6$ is C$_{1-6}$-alkyl.

9. A compound according to claim 1, wherein R$^6$ is C$_{1-6}$-alkyl.

10. A compound according to claim 9, wherein R$^2$ is C$_{1-6}$-alkyl or bromo, and R$^{13}$ is carbaldehyde.

11. A compound according to claim 9, wherein R$^2$ is C$_{1-6}$-alkyl and R$^{13}$ is 1,3-dithiolan-2-yl.

12. A compound according to claim 9, wherein R$^2$ is C$_{1-6}$-alkyl or bromo, and R$^{13}$ is hydroxymethyl.

13. A compound according to claim 9, wherein R$^2$ is C$_{1-6}$-alkyl, chloro or methylthio, and R$^{13}$ is acetyl.

14. A compound according to claim 9, wherein R$^2$ is C$_{1-6}$-alkyl, bromo or chloro, and R$^{13}$ is 1-hydroxyethyl.

15. A compound according to claim 9, wherein R$^2$ is alkyl, bromo, chloro or methylthio, and R$^{13}$ is C$_{1-6}$-alkyl.

16. A compound according to claim 9, wherein R$^2$ is C$_{1-6}$-alkyl, bromo or chloro, and R$^{13}$ is 1-hydroxy-1-methyl-ethyl.

17. A compound according to claim 9, wherein R$^2$ is C$_{1-6}$-alkyl or bromo, and R$^{13}$ is C$_{2-6}$-alkenyl.

18. A compound according to claim 9, wherein R$^2$ is C$_{1-6}$-alkyl and R$^{13}$ is methylthio.

19. A compound according to claim 9, wherein X is sulfur, R$^2$ is chloro, bromo or C$_{1-6}$-alkyl, and R$^{13}$ is C$_{1-6}$-alkyl.

20. A method of treating Parkinson's disease comprising administering to a patient an effective amount of a compound according to claim 1.

21. A composition according to claim 3, wherein said composition contains 0.01–10 mg of said compound.

* * * * *

UNITED STATES PATENT AND TRADEMARK OFFICE
CERTIFICATE OF CORRECTION

PATENT NO. : 5,411,966
DATED : May 2, 1995
INVENTOR(S) : Gerhard SAUER et al.

It is certified that error appears in the above-indentified patent and that said Letters Patent is hereby corrected as shown below:

Claim 1; column 12, line 40: Change "alkyli;" to read - - alkyl; - - .

Signed and Sealed this

Third Day of October, 1995

Attest:

BRUCE LEHMAN

Attesting Officer     Commissioner of Patents and Trademarks